United States Patent [19]

Kumita et al.

[11] 4,004,022
[45] Jan. 18, 1977

[54] SPIROLACTONE DERIVATIVES

[75] Inventors: Izumi Kumita, Oiso; Akiyoshi Ueda, Hiratsuka; Kazuhiko Ohkuma, Ninomiya; Sho Hashimoto, Odawara; Akira Nakada, Hiratsuka; Masami Mizuno, Oiso, all of Japan

[73] Assignee: Nippon Soda Company Limited, Tokyo, Japan

[22] Filed: July 28, 1975

[21] Appl. No.: 599,428

[30] Foreign Application Priority Data

Aug. 9, 1974 Japan .............................. 49-90774

[52] U.S. Cl. .............................. 424/279; 260/343.6
[51] Int. Cl.² ........................................ C07D 307/58
[58] Field of Search ................ 260/343.6; 424/279

[56] References Cited

OTHER PUBLICATIONS

Boyer, et al., Chem. Abst. 73:87514z (1970).
Torii, et al., Chem. Abst. 73:120559t (1970).
Scharf, et al., Angew. Chem. Internat. Edit, vol. 9, (1970), No. 10, p. 810.

Primary Examiner—Henry R. Jiles
Assistant Examiner—C. M. S. Jaisle
Attorney, Agent, or Firm—George B. Oujevolk

[57] ABSTRACT

A compound of the formula

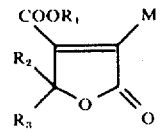

wherein
 $R_1$ is lower alkyl;
 $R_2$ and $R_3$ are methyl, and $R_2$ forms cyclo-alkylene of 5 to 6 carbon atoms by combining with $R_3$;
 M is a substituent selected from the group consisting of $-CH_2X$ and $-CHX_2$ in which X is halogen;
is useful as fungicide.

13 Claims, 1 Drawing Figure

SPIROLACTONE DERIVATIVES

DETAILED DESCRIPTION OF THE INVENTION

Figure 1:
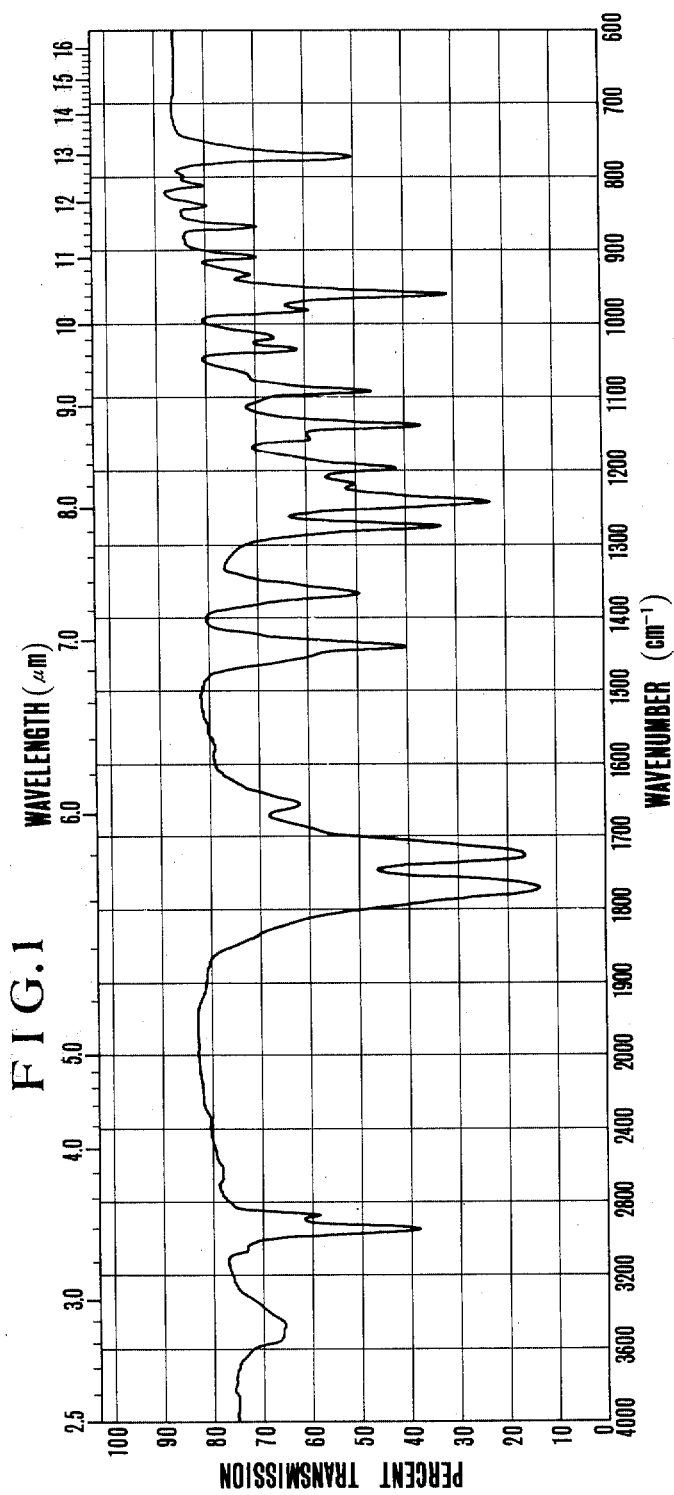

This invention relates to a new compound of spirolactone derivatives, to a process for the preparation thereof and their uses as fungicide.

In particularly this invention relates to new fungicidally active compositions and to method for controlling fungi.

We have discovered that the application of the compounds of this invention by the methods of this invention entirely precludes or reduces damage to plants due to fungi. Fungus mycelia are killed or prevented from developing further by the presence of one or more of the compounds, i.e., the compounds are fungicidal.

It has been found that the above outstanding fungicidal activity can be obtained by applying to the locus of fungus infestation, the compounds represented by the following formula:

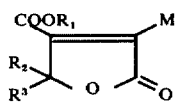

[I]

wherein $R_1$ is lower alkyl;

$R_2$ and $R_3$ are methyl, and $R_2$ forms cyclo-alkylene of 5 to 6 carbon atoms by combining with $R_3$;

M is a substituent selected from the group consisting of $-CH_2X$ and $-CHX_2$ in which X is halogen.

Preferred within the above formula because of its high order of fungicidal activity are:
2-bromomethyl-3-methoxycarbonyl-4-cyclohexanespiro-2-butenolide
2-dibromomethyl-3-methoxycarbonyl-4-cyclohexanespiro-2-butenolide.

The compounds of this invention can be prepared by the following equation:

The above reaction (A) can be conducted in an inert solvent in the presence of an initiator such as benzoyl peroxide or azobisisobutyronitrile.

As an inert solvent, carbon tetrachloride or benzene is used. Ordinarily, temperature from the range of room temperature to boiling point of the employed solvent, and preferably the boiling point, are satisfactory employed. After finishing the reaction, the reaction mixture is cooled and an insoluble material is removed from it by filtration. Then, the filtrate is evaporated under reduced pressure and by recrystallizing the residue from an inert solvent the desired compound can be obtained.

The method of preparation for 2-methyl-3-methoxycarbonyl-4-cycloheranespiro-2-butenolide and 2-methyl-3-methoxycarbonyl-4,4-dimethyl-2-butenolide of the starting material are disclosed in Bull. Chem. Soc. Japan., 35 1194 (1962) and Bulletin de Chimie therapeutique 1970. No. 2, page 105–110.

In order that the invention may be better understood, the following examples are given:

Example 1

2-bromomethyl-3-methoxycarbonyl-4-cyclohexanespiro-2-buternorlde 50 g of 2-methyl-3-methoxycarbonyl-4-cyclohexanespiro-2-butenolide were dissolved in 500 ml of carbon tetrachloride and 43.7 g of N-bromosuccinimide together with 0.5 g of benzoyl peroxide were added to it.

The resulting mixture was maintained during 8 hours at 80° C,. After finishing the reaction, the reaction solution was cooled and an insoluble material was removed from it by filtration. Then, carbon tetrachloride in filtrate was evaporated under reduced pressure and 50 g of the desired compound having a melting point of 86° to 88° C was obtained by recrystallizing the residue from methanol (Yield rate: 73%).

(A):

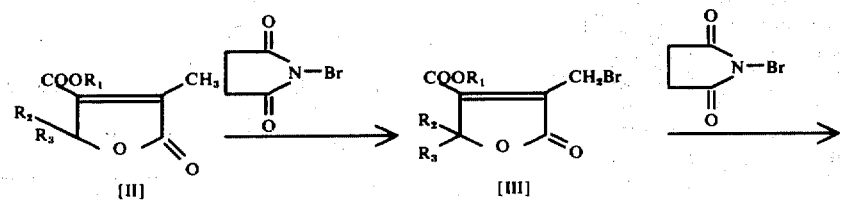

(B):

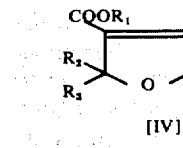

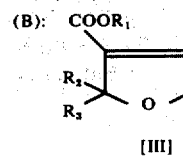

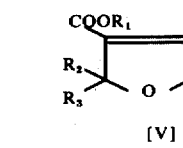

Elemental analysis — Calcd. for $C_{12}H_{15}BrO_4$(%): C: 47.54, H: 5.00, Br: 26.36. Found (%): C: 47.66, H: 4.91, Br: 26.59.

EXAMPLE 2

2-dibromomethyl-3-methoxycarbonyl-4-cyclohexanespiro-2-butenolide 5 g of 2-bromomethyl-3-methoxycarbonyl-4-cyclohexanespiro-2-butenolide were dissolved in 50 ml of carbon tetrachloride and 3.3 g of N-bromosuccinimide together with 40 mg of benzoyl peroxide were added to it. The resulting mixture was maintained during 18 hours at 80° C. After cooling the reaction mixture, an insoluble material was removed from it by filtration and carbon tetrachloride in filtrate was evaporated under reduced pressure.

The product was isolated from the resulting residue by column chromatography and 4.4 g of the purified compound having a melting point of 113 to 116° C was obtained by recrystallizing the crude product from methanol (Yield rate: 70.4%).

Elemental analysis — Calcd. for $C_{12}H_{15}Br_2O_4$(%): C: 37.70 H: 3.66, Br: 41.88. Found (%): C: 37.78, H: 3.57, Br: 42.01.

EXAMPLE 3

2-chloromethyl-3-methoxycarbonyl-4-cyclohexanespiro-2-butenolide 10 g of 2-bromomethyl-3-methoxycarbonyl-4-cyclohexanespiro-2-butenolide was allowed to react with 3.6 g of potassium acetate by refluxing during 3 hours in 40 ml acetic acid.

The reaction solution was poured into water and the resulting aqueous mixture was extracted with ethyl acetate, and further the ethyl acetate layer was washed with the saturated water solution of sodium bicarbonate and water, and then dried with sodium sulfate. After ethyl acetate was concentrated under reduced pressure, 100 ml of methanol containing 5% of hydrochloric acid was added to the residue and it was allowed to stand for overnight at a room temperature.

The resulting solution was concentrated at reduced pressure, the concentrated material was dissolved in ethyl acetate and then the ethyl acetate solution was washed with the water solution of sodium bicarbonate and further with water, and dried with sodium sulfate. After evaporating ethyl acetate at reduced pressure, 3.8 g of 2-hydroxymethyl-3-methoxycarbonyl-4-cyclohexanespiro-2-butenolide having a melting point of 65° to 68° C was obtained by recrystallizing the residue from the mixed solvent of benzene and hexane (1:1).

5 g of the obtained 2-hydroxymethyl-3-methoxycarbonyl-4-cyclohexanespiro-2-butenolide and 1.8 g of pyridine were dissolved in 40 ml of benzene, and then 2.8 g of thionyl chloride was added to it under cooling.

The resulting mixture was maintained during 2 hours at 50° C in a water-bath.

The reaction solution was poured into water and 20 ml of benzene was added to it. The resulting solution mixture was washed with 0.5 normal hydrochloric acid, saturated water solution of sodium bicarbonate and water, and then was dried with sodium sulfate.

The dried solution was evaporated at reduced pressure and 3.5 g of purified 2-chloromethyl-3-methoxycarbonyl-4-cyclohexanespiro-2-butenolide having a melting point of 88° to 90° C was obtained by recrystallizing the residue from the mixed solvent of benzene and hexane (1:1). (Yield rate: 65%).

Elemental analysis — Calcd. for $C_{12}H_{15}ClO_4$(%): C: 55.71, H: 5.84, Cl: 13.70 Found (%) C: 55.58, H: 5.91, Cl: 13.41

Examples of the compounds which can be used in the present invention are listed in Table 1.

Table 1

| Compound No. | Structural Formula | Physical Constant |
|---|---|---|
| 1 | $COOCH_3$, $CH_2Br$ cyclohexane-spiro-butenolide | m.p. 86–88° C |
| 2 | $COOC_2H_5$, $CH_2Br$ cyclohexane-spiro-butenolide | $n_D^{21.5}$ 1.5230 |
| 3 | $COOC_3H_7$, $CH_2Br$ cyclohexane-spiro-butenolide | $n_D^{21.5}$ 1.5221 |
| 4 | $COOC_4H_9$, $CH_2Br$ cyclohexane-spiro-butenolide | $n_D^{21.5}$ 1.5189 |
| 5 | $COOCH_3$, $CHBr_2$ cyclohexane-spiro-butenolide | m.p. 113–116° C |
| 6 | $COOCH_3$, $CHCl$ cyclohexane-spiro-butenolide | m.p. 88–90° C |
| 7 | $COOCH_3$, $CH_2Br$ cyclopentane-spiro-butenolide | $n_D^{24.5}$ 1.5322 |
| 8 | $COOCH_3$, $CH_2Br$ dimethyl-spiro-butenolide | $n_D^{24.5}$ 1.5092 |

As mentioned previously, it has been found that the compounds of the invention posses outstanding fungicidal activity when employed to prevent damage to plants. The paragraphs which follow describe in more detail the utility of this invention.

The compounds of the invention control a wide variety of fungus diseases of foliage, fruit, stems and roots of growing plants without damage to the host.

The many fungi against which the compounds of this invention are active may be represented by, but is not intended to be limited to, the following:
alternaria leaf spot (*Alternaria mali*).
damping-off (*Rhizoctonia solani*),
downy mildew (Preudoperonospora cubensis),
clown rust (*Puccilia coronata*)
fusarium wilt (*Fusarium cucumerium*),
late blight (*Phytophthora capsis*),
canker (*Xanthomonas citri*), bacterial canker (*Corynebacterium michiganse*)
bakanae disease (*Gibberella fujikuroi*),
blast (*Phyricularia oryzae*)
sheath blight (*Pellicularia sasaki*)
helminthosporium leaf spot (*Cochliobolus miyabeanus*)
and particularly effective against fusarium wilt, downy mildew and clown rust.

It is another advantage that the compounds of the present invention have low toxicity for warm-blooded animals and fish.

The method of the present invention comprehends the employment of a liquid or solid composition containing one or more of the present compounds as an active component.

The compound can be used directly without mixing with suitable carriers.

The active ingredient of this invention may be formulated by mixing with suitable carriers in a form generally used in pesticidal compositions such as wettable powder, emulsifiable concentrate, dust formulation, granular formulation, water soluble powder and aerosol. As solid carriers, bentonite, diatomaceous earth, apatite, gypsum, talc, pyrophyllite, vermiculite, clay and others are used. As liquid carriers, kerosene, mineral oil, petroleum, solvent naphtha, xylene, cyclohexane, cyclohexanone, dimethylformamide, dimethylsulfoxide, alcohol, acetone, benzene and others are used. Sometimes surface active agent is added in order to give a homogenous and stable formulation.

The concentrations of the active ingredients in the fungicidal composition of this invention vary according to type of formulation and they are, for example, used in a range of 5 – 80 weight percent, preferably 20 – 80 weight percent, in wettable powders, 5 – 70 weight percent, preferably 10 – 50 weight percent, in emulsifiable concentrates, and 0.5 – 20 weight percent, preferably 1 – 10 weight percent in dust formulations.

Incidentally, wettable powder or emulsifiable concentrate containing proper quantity of the active compound is suspended or emulsified in water and then sprayed to the foliages of the plants or on the locus to be protected. Furthermore, the compounds may be used as a mixture with other fungicides, insecticides, acaricides and herbicide.

Some examples in this invention are stated below. But the main compounds and the additives are not defined limitedly by these Examples.

EXAMPLE 4

Wettable Powder

|  | Parts by weight |
|---|---|
| Compound No. 1 | 20 |
| Sodium alkylsulfonate | 6 |
| Diatomaceous earth | 37 |
| Talc | 37 |

These are mixed homogeneously and reduced to fine particles. Consequently, wettable powder containing 20% of the active ingredient is obtained. In practical use, it is diluted to a certain concentration with water and is sprayed as a suspension.

EXAMPLE 5

Emulsifiable Concentrate

|  | Parts by weight |
|---|---|
| Compound No. 2 | 40 |
| Polyoxyethylenealkylarylether | 10 |
| Xylene | 35 |
| Dimethylformamide | 15 |

These are mixed and dissolved. Consequently, emulsifiable concentration containing 40% of the active ingredient is obtained. In practical use, it is diluted to certain concentration with water and then is sprayed as an emulsion.

EXAMPLE 6

Dust Formulation

|  | Parts by weight |
|---|---|
| Compound No. 3 | 10 |
| Talc | 90 |

These are mixed homogeneously, reduced to fine particles. Consequently, dust formulation containing 10% of the active ingredient is obtained. In practical use, it is directly applied.

The superior fungicidal activity of compounds of this invention is clearly illustrated by the following tests.

Test 1. Test for Control of Alternaria leaf spot

Apples leaves were cut off from the potted apple plant (variety: starking) and the detached leaves were immersed during 30 to 60 seconds into the diluted solution of a specified concentration of wettable powder containing test compound.

After air-drying, the leaves were inoculated with the spore suspension of *Alternaria mali* in the concentration of 200,000/ml and incubated in a wet chamber at 28° C.

One day after innoculation, an average number of lesions was examined and evaluation of percent disease was calculated control on the basis of number of lesions occuring on the untreated check.

The state of inhibiting against the germinating of spore on leaves was also observed through a microscope. The result was shown in Table 2.

Table 2

| Test Compound | Concentration of active ingredient (ppm) | Control Value (%) | State of inhibition of spoer germination |
|---|---|---|---|
| 1 | 250 | 100 | ± |
|  | 125 | 95 | + |
|  | 62.5 | 85 | − |
| 2 | 250 | 50 | ± |
| 3 | 250 | 50 | ± |
| 5 | 250 | 82.5 | ± |
| Polyoxins ** | 125 | 88 | + |
| (10% wettable powder) | 62.5 | 65 | ± |
|  | 31.3 | 50 | − |
| Captafol *** | 800 | 100 | + |
| (10% wettable powder) | 400 | 100 | + |
|  | 200 | 100 | + |

Table 2-continued

| Test Compound | Concentration of active ingredient (ppm) | Control Value (%) | State of inhibition of spoer germination |
|---|---|---|---|
| Untreated | — | 0 | — |

* degree for state of inhibition of spore germination:
  —: normal germination
  ±: abnormal germination
  +: inhibition of spore germination
** A series of antibiotic substances produced in culture solution of a Japanese *Streptomyces Cacaoi Var Asoensis* species.
*** cis-N[(1,1,2,2-tetrachloroethyl)thio]-4-cyclohexene-1,3-dicarboximide

Test 2. Pot Test for Control of Alternaria leaf spot

The potted young apple plants (Star King) were sprayed, at a rate of 100 ml. per plant, with an aqueous suspension having a concentration of 500, 250 and 125 ppm of an active ingredient which suspension was prepared by diluting a wettable powder with water to a specified concentration. Young branches having about 7 to 8 leaves were cut off from each tree and leaves were also cut off from tree after allowing to stand for 1 day, 3 days and 7 days in green-house after the spraying of above suspension, and then inoculated with spore suspension of *Alternaria mali*, and held under the condition of incubation for 24 hours in a wet chamber. Then, average number of lesions per branch was counted and evaluation of percent disease control was calculated on the base of number of lesions occurring on the untreated check. The state of inhibition of spore germination leaf was also obserbed.

Table 3

| Test Compound | Concentration of active ingredient (ppm) | Control Value (%) Time between spraying and inoculation (days) | | | | | |
|---|---|---|---|---|---|---|---|
| | | detucled branch | | | leaf | | |
| | | 1 | 3 | 7 | 1 | 3 | 7 |
| 1 (50% wettable powder) | 500 | 99 | 100 | 22 | 100+ | 75+ | 50— |
| | 250 | 100 | 99 | 10 | 100+ | 95± | 45— |
| | 125 | 99 | 33 | 6 | 78± | 30— | 25— |
| Polyoxins (10% wettable powder) | 100 | 100 | 100 | 100 | 100+ | 100+ | 100± |
| Captafol (80% wettable powder) | 800 | 100 | 100 | 100 | 100+ | 98_ | 100+ |
| Untreated | — | 0 | 0 | 0 | 0— | 0— | 0— |

Test 3. Test for Control of Canker

Leaves were cut off from the potted young plants of summer orange and they were made a little holes.

The detailed leaves were immersed during 32 to 60 seconds into the diluted solution of a specified concentration of wettable powder containing test compound.

After air-drying, the leaves inoculated with the spore suspension of Xanthomonas citri in the concentration of $10^{7-8}$ cells/ml and incubated in a wet chamber at 28° C.

Seven days after inoculation, a number of lesions was examined and evaluation of percent disease control was calculated on the basis of number of lesions occuring on the untreated check.

The result was shown in Table 4.

Table 4

| Test Compound | Concentration of active ingredient (ppm) | Control Value (%) | Phytotoxicity |
|---|---|---|---|
| 1 | 250 | 93 | none |

Table 4-continued

| Test Compound | Concentration of active ingredient (ppm) | Control Value (%) | Phytotoxicity |
|---|---|---|---|
| 5 | 250 | 89 | none |
| 8 | 250 | 91 | none |
| dihydrostreptomycine-sulfate | 200 | 91 | none |
| Comparative compound CQOCH₃ / CH₃ (cyclohexene structure) | 250 | 50 | +* |
| Untreated | 0 | 0 | none |

*+: necropic spot

Test 4. Pot test for Control of Canker

A summer orange plant was grown in a pot. 40 ml of an aqueous suspension prepared by diluting a wettable powder to a specified concentration was sprayed on the two pots and these pots were allowed to stand in a green-house. One day after spraying, summer orange plants were inoculated with the spore suspension of *Xanthomonas citri* in the concentration of $10^{7-8}$ cells/ml and incubated in a wet chamber at 28° C during a day. About 3 weeks after keeping said pots in a green-house, the disease degree of new leaves was examined and evaluation of percent disease control as calculated on the base of the disease degree on the untreated check.

The result was shown in Table 5.

Table 5

| Test Compound | Concentration of active ingredient (ppm) | Control Value (%) |
|---|---|---|
| 1 | 1000 | 81 |
| | 500 | 50 |
| 8 | 500 | 58 |
| dihydrostreptemycine sulfate | 200 | 87 |
| Untreated | — | 0 |

Test 5. Test for Control of Damping-off

Cucumber was grown in pots.

10 g of culture medium consisting of the mash and chaff in which *Rhizoctonia solani*, has been cultured was mixed with 300 g of normal soil. 20 g of said mixture was put in a pot when cotyledon of cucumber was developed and 10 ml of water diluted solution of the wettable powder containing the test compound was poured in the pot at a rate of 2.6 liters per one square meters.

Five days later, a disease count was made and evaluation of percent disease control was based on the percentage of disease on the untreated chock. Each test was repeated three times for each concentration. The results was shown in Table 6.

Table 6

| Test Compound | Concentration of active ingredient | Control Value (%) |
|---|---|---|
| 1 | 250 | 100 |
| 2 | 250 | 100 |
| 3 | 250 | 71 |
| 5 | 250 | 100 |
| 6 | 250 | 100 |
| 7 | 250 | 100 |
| 8 | 250 | 100 |
| Comparative compound | | |
| 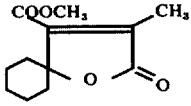 | 250 | 0 |
| 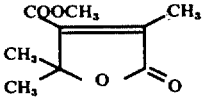 | 250 | 0 |
| PCNB* | 250 | 100 |
| Untreated | — | 0 |

*: pentachloronitrobenzene

Test 6. Test for Control of Late blight

Tomato leaves were cut off from the potted tomato (variety: Oogatafukuju) and the detached leaves were immersed during 30 to 60 seconds into the diluted solution of a specified concentration of wettable powder containing test compound. After air-drying, the leaves were inoculated with the zoospore suspension of late blight (*Phytophthora capsici*) in the concentration of 30,000/ml and incubated in a green-house at 28° C. Two days after inoculation, the disease degree was examined and evaluation of percent disease control was calculated on the disease degree of untreated check. The results were shown in Table 7.

Table 7

| Test Compound | Concentration of active ingredient (ppm) | Control Value (%) |
|---|---|---|
| 1 | 250 | 100 |
| 2 | 250 | 96 |
| 3 | 250 | 100 |
| 4 | 250 | 100 |
| 5 | 250 | 100 |
| 8 | 250 | 100 |
| Comparative compound | | |
| 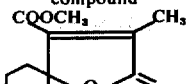 | 250 | 0 |
| Captan* | 250 | 100 |
| Untreated | — | 0 |

* cis-N[(trichloromethyl)thio]-4-cyclohexene-1,3-dicarboximide

Test 7. Test for Control of Downy mildew

Cucumber leaves (variety: Satsukimidori) were cut off and the detached leaves were immersed during about 30 seconds in the diluted solution having a specified concentration of test compound. After air-drying, the leaves were inoculated with the spore suspension of *Pseudoperonospora cubensis* in the in the concentration of 5 × 10⁴/ml.

Eight days after keeping them in a wet chamber by exposing to light, the degree of disease was examined and evaluation of percent disease control was calculated on the disease degree of the untreated check.

The result was shown in Table 8.

Table 8

| Test Compound | Concentration of active ingredient (ppm) | Control Value (%) |
|---|---|---|
| 6 | 250 | 100 |
| 8 | 250 | 55 |
| Untreated | — | 0 |

Test 8. Pot test for Control of Downy mildew 20 ml/pot of the diluted solution having a specified concentration of test compound was sprayed on the both side of the potted cucumber leaves and further the spore suspension of *Pseudoperonospora cubensis* in the concentration of 7 × 10⁴/ml was inoculated on the back of leaves after allowing to stand for a specified day. Eight to ten days after keeping the pot at 23° C, a number of lesions and disease area were examined and evaluation of purcent disease control was calculated on the disease degree of the untreated check.

The result was shown in Table 9.

Table 9

| Test Compound | Concentration of active ingredient (ppm) | Time between spraying and inoculation (days) | Control Value (%) |
|---|---|---|---|
| 6 | 500 | 1 | 100 |
| | | 4 | 95 |
| | | 7 | 45 |
| 8 | 500 | 1 | 100 |
| | | 4 | 99 |
| | | 7 | 37 |
| triazine | 500 | 1 | 100 |
| | | 4 | 99 |
| | | 7 | 90 |
| Untreated | — | 1 | 0 |
| | | 4 | 0 |
| | | 7 | 0 |

An explanation of the drawing:

FIG. 1 is the infrared spectrum of 2-bromomethyl-3-methoxycarbonyl-4-cyclohexanespiro-2-butenolide.

What is claimed is:

1. 2-bromomethyl-3-methoxycarbonyl-4-cyclohexanespiro-2-butenolide.

2. A fungicidal composition comprising an inert carrier and a fungicidally effective amount of a compound of the formula

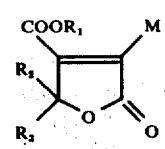

wherein
$R_1$ is lower alkyl;
$R_2$ and $R_3$ are methyl, or $R_2$ forms cyclo-alkylene of 4 to 5 carbon atoms by combining with $R_3$;

M is a substituent selected from the group consisting of —CH₂X and —CHX₂ in which X is halogen.

3. A fungicidal composition comprising an inert carrier and a fungicidally effective amount of a compound of the formula

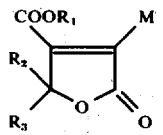

wherein
R₁ is alkyl of 1 to 4 carbon atoms;
R₂ and R₃ are methyl, or R₂ forms cyclo-alkylene of 4 to 5 carbon atoms by combining with R₃;
M is a substituent selected from the group consisting of —CH₂X and —CHX₂ in which X is selected from the group consisting of chlorine and bromine.

4. A fungicidal composition comprising an inert carrier and a fungicidally effective amount of a compound of the formula

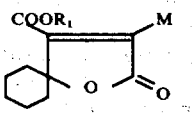

wherein
R₁ is alkyl of 1 to 4 carbon atoms;
M is a substituent selected from the group consisting of —CH₂X and —CHX₂ in which X is bromine.

5. A fungicidal composition comprising an inert carrier and a fungicidally effective amount of 2-bromomethyl-3-methoxycarbonyl-4-cyclohexanespiro-2-butenolide.

6. A fungicidal composition comprising an inert carrier and a fungicidally effective amount of 2-dibromomethyl-3-methoxycarbonyl-4-cyclohexanespiro-2-butenolide.

7. A method of killing fungi on plants comprising applying to said fungi or the locus thereof, a fungicidally effective amount of a compound of the formula

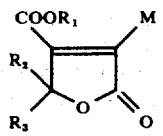

wherein
R₁ is lower alkyl;
R₂ and R₃ are methyl, or R₂ forms cyclo-alkylene of 4 to 5 carbon atoms by combining with R₃;
M is a substituent selected from the group consisting of —CH₂X and —CHX₂ in which X is halogen.

8. A method of killing fungi on plants comprising applying to said fungi or the locus thereof, a fungicidally effective amount of a compound of the formula

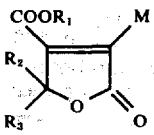

wherein
R₁ is alkyl of 1 to 4 carbon atoms;
R₂ and R₃ are methyl, or R₂ forms cyclo-alkylene of 4 to 5 carbon atoms by combining with R₃;
M is a substituent selected from the group consisting of —CH₂X and —CHX₂ in which X is selected from the group consisting of chlorine and bromine.

9. A method of killing fungi on plants comprising applying to said fungi or the locus thereof, a fungicidally effective amount of a compound of the formula

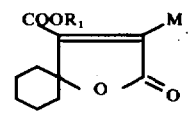

wherein
R₁ is alkyl of 1 to 4 carbon atoms;
M is a substituent selected from the group consisting of —CH₂X and —CHX₂ in which X is bromine.

10. A method of killing fungi on plants comprising applying to said fungi or the locus thereof, a fungicidally effective amount of 2-bromomethyl-3-methoxycarbonyl-4-cyclohexanespiro-2-butenolide.

11. A method of killing fungi on plants comprising applying to said fungi or the locus thereof, a fungicidally effective amount of 2-dibromomethyl-3-methoxycarbonyl-4-cyclohexanespiro-2-butenolide.

12. A process for the production of a compound of the formula

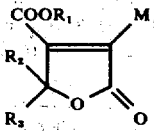

wherein
R₁ is lower alkyl;
R₂ and R₃ are methyl, or R₂ forms cyclo-alkylene of 5 to 6 carbon atoms by combining with R₃;
M is a substituent selected from the group consisting of —CH₂X and —CHX₂ in which X is bromine;
which comprises reacting a compound of the formula

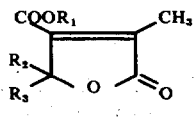

wherein R₁, R₂ and R₃ represent the aforesaid meanings, with N-bromosuccinimide in the presence of benzoylperoxide or azobisisobutyronitrile.

13. A process for the production of a compound of the formula

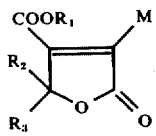

wherein
R₁ is lower alkyl;
R₂ and R₃ are methyl, or R₂ forms cyclo-alkylene of 5 to 6 carbon atoms by combining with R₃;

M is substituent selected from the group consisting of —CH₂X and —CHX₂ in which X is chlorine; which comprises reacting a compound of the formula

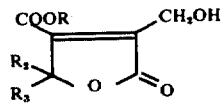

wherein R₁, R₂ and R₃ represent the aforesaid meanings, with thionyl chloride, phosphorus trichloride or phosphorus pentachloride.

* * * * *